United States Patent [19]

Perlin

[11] Patent Number: 4,726,372

[45] Date of Patent: Feb. 23, 1988

[54] HEMOSTATIC CLIP

[75] Inventor: Alfred R. Perlin, Highland Park, Ill.

[73] Assignee: Metatech Corporation, Wheeling, Ill.

[21] Appl. No.: 909,241

[22] Filed: Sep. 19, 1986

[51] Int. Cl.[4] .............................................. A61B 17/12
[52] U.S. Cl. .................................... 128/325; 128/326; 128/346
[58] Field of Search ...................... 128/325, 326, 346; 24/543, 563, 489

[56] References Cited

U.S. PATENT DOCUMENTS

| 3,822,052 | 7/1974  | Lange          | 24/543  |
| 3,926,195 | 12/1975 | Bleier et al.  | 128/346 |
| 4,227,730 | 10/1980 | Alexander et al. | 128/346 |
| 4,346,869 | 8/1982  | MacNeill       | 128/346 |
| 4,390,019 | 6/1983  | LeVeen et al.  | 128/346 |
| 4,418,694 | 12/1983 | Beroff et al.  | 128/346 |
| 4,424,810 | 1/1984  | Jewusiak       | 128/346 |
| 4,449,531 | 5/1985  | Cerwin et al.  | 128/346 |
| 4,643,389 | 2/1987  | Elson et al.   | 24/543  |

Primary Examiner—C. Fred Rosenbaum
Assistant Examiner—Gene B. Kartchner

[57] ABSTRACT

A surgical clamp for clamping a blood vessel and preferably made of a single piece of plastic material is provided with a hinge element flexibly connecting one end each of an upper and lower clamping arm at a spaced distance. The other end of one of the clamping arms has a locking pawl flexibly connected thereto. A mating locking mechanism flexibly connected to the other of the clamping arms engages a latch pin on the locking pawl when the clamping arms are brought together. The four hinge points, including the point of juncture between latch pin and the locking mechanism, are arrayed in a parallelogram configuration which provides for parallel movement and automatic self adjustment of the distance between the clamping arms as the clamping arms are brought together to clamp the blood vessel. Combined flexible wall and locking mechanism elements prevent the blood vessel from being dislodged after the clamping operation, and provide ease of application of the clamp to the blood vessel.

11 Claims, 10 Drawing Figures

HEMOSTATIC CLIP

The present invention relates to a hemostatic clip, which is a surgical clamp for stopping the flow of blood from a blood vessel during surgical procedures. In particular, the invention relates to a surgical clamp having a novel parallelogram hinged structure to provide automatic adjustment for clamping various sizes of blood vessels without damaging the vessel, and positive stop elements to prevent a vessel from being pinched or rolling out of the clamp.

During certain surgical procedures, it becomes necessary to occlude or tie off an artery. This may be occasioned by the artery requiring repair, cleaning, or the desire to anastomose it to another blood vessel. Occluding a blood vessel also maintains the surgical site free of an excess of blood and reduces blood loss in the patient. Where the removal of a tumor or organ is required, it becomes necessary to separate the tumor or organ from certain vessels, and prior to separating the vessels must be ligated, or occluded.

When a blood vessel is closed off, the body reacts naturally by continuing to allow the flow of blood around the occluded area through secondary vessels, where the natural physiological function of the body enlarges these by-pass vessels until adequate blood flow is achieved Therefore, when occluding a vessel, there should be a positive clamping of the vessel, without leakage, to prevent blood loss in the patient and disruption of the natural hemostasis and production of alternate paths of blood flow in the patient.

Usually, the occluding of a blood vessel during surgery is accomplished using an occluding clamp which must be designed to gently but positively squeeze the vessel, and at the same time evenly compress the vessel without injury. Also, after the clamp is applied, it should be void of openings or other surfaces through which the vessel could be accidently dislodged from the clamp or pinched, which could result in a serious loss of blood. The pressure applied by the clamp must be even, so as not to damage the surface of the vessel by abrasion.

Since the blood vessels in the body vary in overall diameter, a clamping device must be suitable to apply a positive, but gentle non-injurious pressure to vessels of varying sizes. With larger vessels, the gap between the clamping arms will be greater, but the pressure applied must be uniform so as not to sever or puncture the closed vessel. If the clamp is not adjustable to account for various sized vessels, clamps of several different sizes must be provided to a surgical team. While certain clamps that are presently available are adjustable, the surgeon must estimate the proper point of adjustment, with the possibility of an inaccurate estimate which results in severing or puncturing the vessel. An example of a clamp of this type is shown in U.S. Pat. No. 4,390,019, which includes a ratchet-type locking device in a blood vessel clamp. In the device disclosed in that patent, the person applying the clamp must make a conscious decision as to the proper clamping pressure to select through use of the ratchet. This can be a difficult decision to make, particularly where clamps of the type under discussion are usually inserted by a forceps-type applying instrument, and the surgeon may not be able to directly get the feel of the clamping pressure as it is being applied.

Other presently available occluding clamps, such as those shown in U.S. Pat. Nos. 4,418,694; 4,449,531; 4,424,810 and 3,926,195, make no provision for adjustment to accomodate the clamping of blood vessels of varying sizes. Further, these patents do not disclose an automatically adjustable occluding clamp to receive blood vessels of varying sizes, in combination with elements which prevent a vessel from being pinched in the hinge segments of the clamp and from being dislodged from the clamp during and subsequent to the clamping operation. The present invention overcomes these shortcomings in existing clamps, and does so in a clamp construction which is readily and simply manufactured at inexpensive production costs.

A primary object of the present invention is to provide a novel construction for an occluding clamp which is automatically self-adjustable and flexible enough to allow the clamp to accommodate blood vessels of varying sizes.

Another object of the present invention is to provide an occluding clamp having a hinge structure which automatically permits a pre-established force to be applied by the clamp to a blood vessel regardless of the size of the blood vessel.

A further object of the present invention is to provide an occluding clamp for surgical procedures having a combined positive lock and forward stop element which permits the clamp to be easily and positively locked when clamped to a blood vessel while at the same time preventing the vessel from being dislodged from the clamp.

An important object of the present invention is to provide a novel four pivot point hinge mechanism in a blood vessel clamp, in combination with elements which prevent the blood vessel from being pinched in the hinge mechanism.

Still another object of the present invention is to provide a blood vessel clamp allowing ease of entry of the blood vessel between the clamping arms by rotating a locking arm between a vessel entry position and a locking position.

In the preferred embodiment of the invention, the above objectives are accomplished in an occluding clamp desireably made from one piece of a plastic material. A pair of clamping arms are connected at one end by a hinge element, wherein each of the clamping arms is connected to the hinge element at separate, spaced hinge points. A rear wall element is fixed to one of the clamp arms to prevent pinching the blood vessel between the clamping arms and the hinge element. The other end of the lower clamp arm includes a combined locking mechanism and forward wall hinged to the lower arm to allow the upper clamp arm to be locked to and unlocked from the lower clamp arm, and to provide a wall to stop the clamped blood vessel from being dislodged from the clamp. The other end of the upper clamping arm has hinged thereto a depending locking pawl adapted to mate with the locking mechanism of the lower arm when a blood vessel is clamped between the arms. The four hinge points at both ends of the upper and lower clamp arms are arranged in a parallelogram configuration which provides automatic adjustment of the clamping device as the device clamps vessels of varying sizes. This parallelogram hinge configuration also provides a smoothly tapered curve when clamping force is plotted against opening size, thereby providing a pre-selected blood vessel clamping force at any given opening dimension. The hinged connection between the locking mechanism and the lower clamping arm permits the locking mechanism to be pivoted out of the way when a blood vessel is being inserted, and then to be pivoted back into position for locking when the blood vessel is properly between the clamping arms.

Other objects and advantages of the present invention will be apparent from the following detailed description of the preferred embodiments thereof, which description should be considered in conjunction with the accompanying drawings in which.

Figure 1:
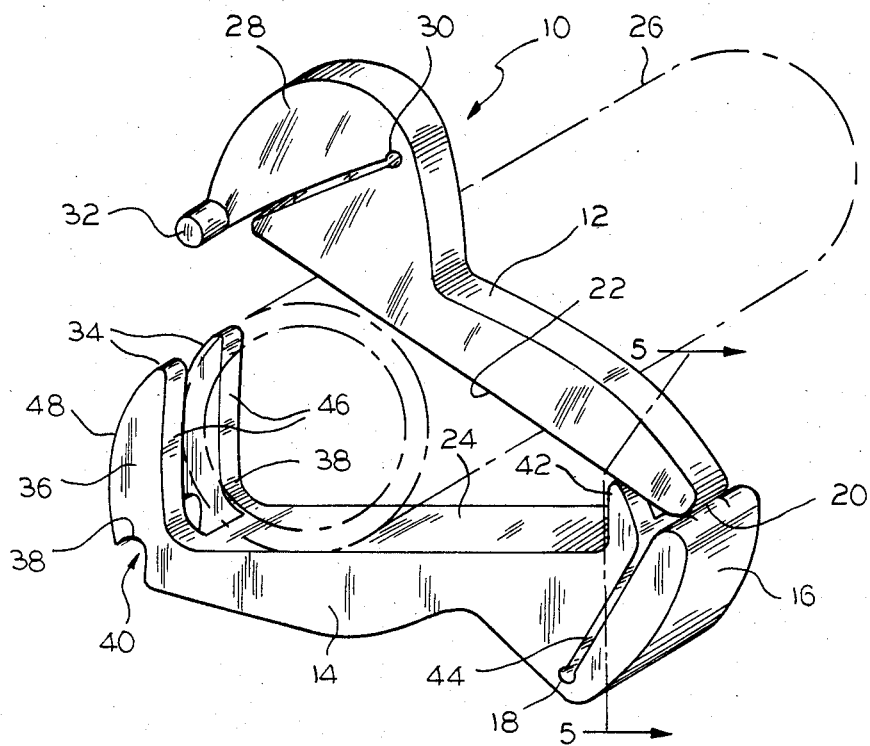
FIG. 1 is a perspective view of one embodiment of the blood vessel clamping device of the present invention, shown in its open position.

In the embodiment of the invention illustrated in FIGS. 1-7, the clamp 10 comprises several segments including an upper clamping arm 12 and a lower clamping arm 14. At the right end of clamp 10, as viewed in FIGS. 1-3, the upper and lower clamp arms 12, 14 are joined by another segment comprising a flexible hinge element 16, which is part of the one piece of plastic material from which clamp 10 is fabricated. Lower clamping arm 14 is flexibly connected to hinge 16 at a first hinge point 18, and upper clamping arm 12 is flexibly connected to hinge 16 at second hinge point 20.

Figure 3:
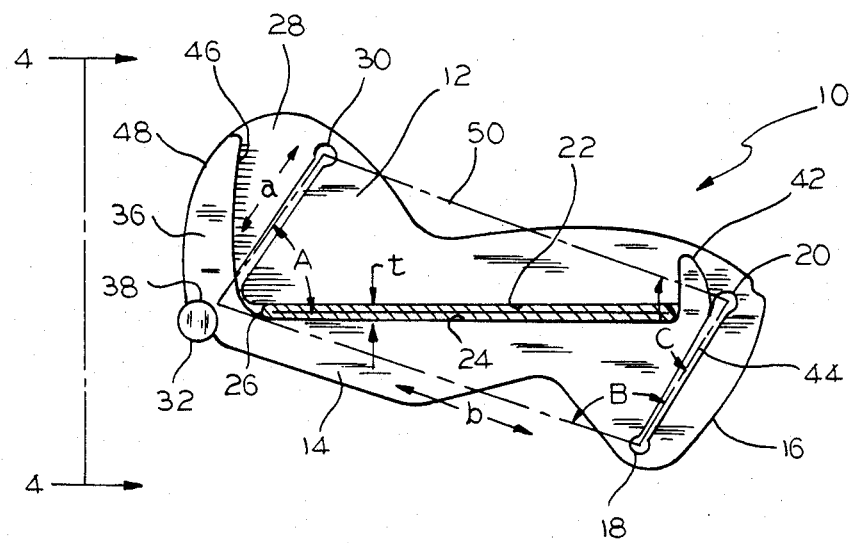
FIG. 3 is a side elevation view of the clamping device of FIG. 1, shown in its closed and locked position with a blood vessel clamped between the clamping arms.

The mating portions of arms 12 and 14 comprise relatively smooth, straight clamping surfaces 22, 24, respectively, which are adapted to engage and clamp blood vessel 26 when the clamp 10 is in the position illustrated in FIG. 3.

The left end of upper clamping arm 12 is provided with another segment, namely locking pawl 28 flexibly connected to arm 12 at a third hinge point 30. Pawl 28 terminates with a latch pin 32 protruding laterally from the pawl.

Figure 4:
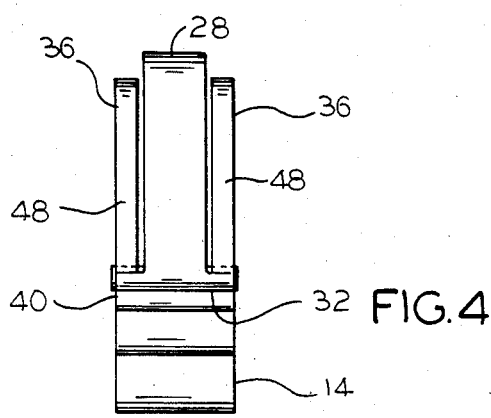
FIG. 4 is a front elevation view of the clamping device of FIGS. 1-3, taken along line 4—4 of FIG. 3.
Figure 5:
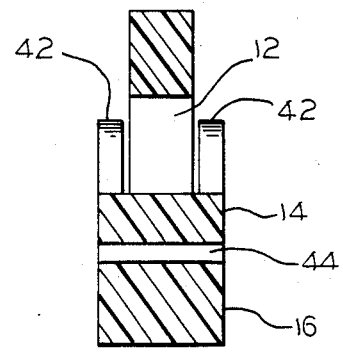
FIG. 5 is a section elevation view of the clamping device of FIG. 1 taken along line 5—5.

As best seen in FIGS. 1, 4, and 5, the lateral dimension of upper clamping arm 12 is less than that of lower clamping arm 14, and upper clamping arm 12 is centrally disposed at second hinge point 20 where it is flexibly joined to hinge element 16. The purpose of this dimensional variation is to enable locking pawl 28 to extend between the two parallel upright arms 34 of locking mechanism 36, which arms 34 are flexibly attached to lower clamping arm 14 at a pair of fourth hinge points 38. Fourth hinge points 38 permit arms 34 to rotate approximately ninety degrees about fourth hinge point 38 to enable ease of insertion of vessel 26 into clamp 10, as will be more fully explained. Fourth hinge points 38 include indentations 40 which are adapted to receive latch pin 32 when clamp 10 is in its closed position (FIGS. 2, 3), and hold the clamp closed.

At the portion of lower clamping arm 14 adjacent hinge 16, a pair of rear wall elements 42 are integrally formed with the lower clamping arm for the purpose of preventing blood vessel 26 from being pinched in the gap 44 between hinge element 16 and lower clamping arm 14. Rear wall 42 also prevents the portion of the blood vessel adjacent hinge element 16 from being pinched between clamping arms 12 and 14 during the initial stages of the clamping operation, and before the arms 12, 14 are moved parallel to each other, as will be explained. As seen in FIG. 5, rear wall elements 42 are disposed on either side of upper clamping arm 12.

Integral with locking mechanism 36 are a pair of forward wall surfaces 46 which extend upward from clamping surface 24 of lower clamping arm 14. In the closed position of clamp 10 (FIGS. 2, 3), wall surfaces 46 extend laterally on either side of locking pawl 28 and prevent blood vessel 26 from being dislodged or accidently removed from clamp 10 when the clamp is locked.

In use, clamp 10 is placed adjacent a blood vessel 26 to be occluded (FIG. 1) by means of an applying instrument or by hand, such that the vessel 26 extends between the opening between upper clamping arm 12 and lower clamping arm 14. Pressure is then applied to the clamping arms until they are brought together such that vessel 26 is constricted between the clamping arms (FIG. 3). As upper clamping arm 12 is brought towards lower clamping arm 14, latch pin 32 comes into contact with, and glides along curved outer surface 48 of locking mechanism 36 until the latch pin engages and is grasped by indentation 40 to lock the upper and lower clamping arms 12, 14 together with blood vessel 26 therebetween. To release the clamp, if necessary, latch pin 32 is disengaged from indentation 40 and the upper and lower clamping arms 12, 14 are pivoted about first and second hinge points 18, 20 until they reach the position shown in FIG. 1.

An important aspect of the present invention is the relationship between hinge points 18, 20, 30 and 38, which form a parallelogram as shown by the dotted line 50 in FIG. 3. As a result of this parallelogram relationship between the hinge points, four pivot points are provided when the clamp is closed over a blood vessel. This enables the clamp 10 to automatically adjust itself to accommodate blood vessels of different thicknesses by varying the included angle between adjacent segments of the clamp 10, as the gap t (FIG. 3) between clamping surface 22 and clamping surface 24 adjusts to receive a blood vessel having a specific thickness when the clamp is applied to a blood vessel. This is accomplished wherein, as clamp 10 is closed over a blood vessel 26, the upper clamping arm 12 ostensibly pivots about both hinge points 18 and 20 as more pressure is applied, thereby altering the included angles B and C (FIG. 3), and allowing the distance between the clamping arms to increase, if necessary, as hinge element 16 is displaced in a counter-clockwise direction about hinge point 18. As the distance t becomes automatically established as a function of the thickness of the blood vessel 26, locking pawl 28 pivots about hinge point 30 as latch pin 32 glides along curved outer surface 48 of locking mechanism 36. This enables the left side of clamp 10 (FIGS. 2, 3) to automatically adjust to the thickness of blood vessel 26 as the clamp moves to its locked position.

During experimentation, it has been found that the parallelogram hinge point configuration of the clamp 10 provides optimum results when (a) the included angle A between hinge points 30, 38 and hinge points 38, 18 is greater than or equal to 50°, and less than or equal to 85°, (b) the included angle B between hinge points 20, 18 and 18, 38 is between 95° and 130°, and (c) the linear ratio a/b of the distance a between hinge points 30, 38 and the distance b between hinge points 38, 18 is greater or equal to 0.25 and is less than or equal to 0.85.

The parallelogram hinge point configuration of the present clamping device, besides allowing automatic adjustment of the distance t between clamping surfaces 22, 24, also permits the clamp 10 to provide a smooth clamping action when applied, which lessens the possibility that the blood vessel will be accidently punctured or severed. When plotting applied clamping force against the distance t between clamping surfaces, a smoothly tapered curve results. This means that by constructing the physical attributes of the elements of clamp 10 surrounding hinge points 18, 20, 30 and 38, the clamp will apply a pre-established, known pressure force to the blood vessel at all values of the opening t. Thus, a single clamp design can be utilized to occlude blood vessels over a wide range of thicknesses.

The parallelogram structure set forth above also enables the clamping surfaces 22, 24 of the clamping arms 12, 14 respectively, to move parallel to each other during the full range of a clamping operation. This greatly reduces the possibility of injuring or severing the blood vessel.

When clamp 10 is being used in a constricted space, the structure surrounding hinge point 38 permits ease of application of the clamp to a blood vessel. If desired, locking mechanism 36 is pivoted ninety degrees counter-clockwise about fourth hinge point 38 until forward wall surface 46 is substantially co-planar with clamping surface 24. The blood vessel is then guided into the opening between clamping arms 12 and 14, and locking mechanism 36 is then rotated ninety degrees in the other direction until it is in the position shown in FIG. 1. The clamp 10 is then closed and locked over the vessel 26 as described above.

Figure 6:
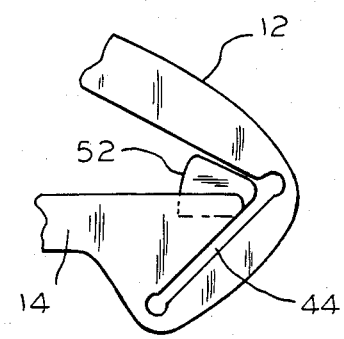
FIGS. 6 and 7 are detailed views showing a modified version of the clamping device of FIGS. 1-5, illustrating the disposition of an embodiment of a vessel guard element to prevent pinching of the blood vessel by the rear hinge element.
Figure 7:
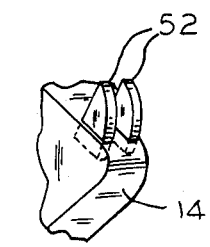

FIGS. 6 and 7 disclose a modified version of the clamp of FIGS. 1-5, wherein rear wall elements 42 are replaced with a pair of vessel guards 52 which are embedded in lower clamping arm 14. Vessel guards 52 prevent the blood vessel from moving too far to the right, as viewed in FIGS. 1-3, during the clamping operation, and thereby prevent the portion of the blood vessel adjacent hinge element 16 from being pinched during the initial stages of the clamping operation and before the full effect of the parallelogram direction of movement of the clamping arms is effected.

Figure 8:
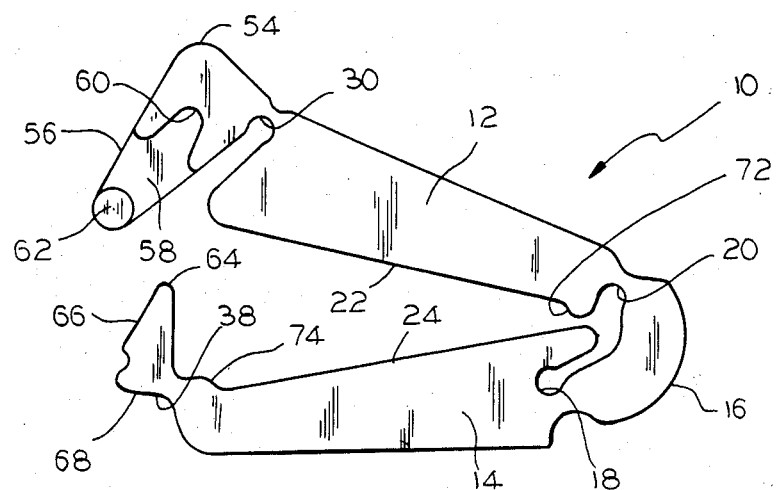
FIG. 8 is a side elevation view of a second embodiment of the blood vessel clamping device of the present invention, shown in the open position wherein the locking mechanism and pawl is differently configured.
Figure 9:
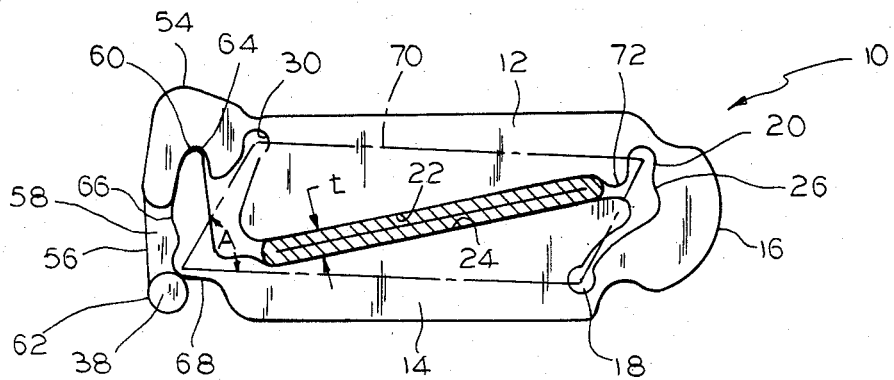
FIG. 9 is a side elevation view of the clamping device of FIG. 8 shown in the clamped position around a blood vessel of relatively small size.
Figure 10:
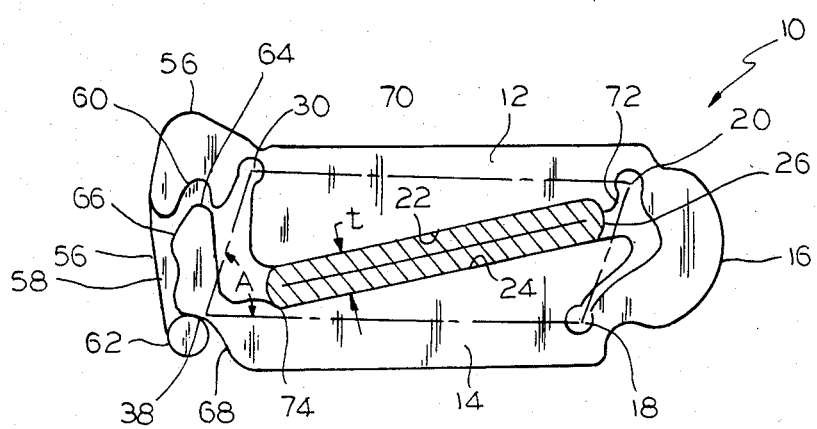
FIG. 10 is a side elevation view of the clamping device of FIGS. 8 and 9, shown clamped around a blood vessel of relatively larger size.

A second embodiment of the present invention is disclosed in FIGS. 8, 9 and 10, wherein like reference numerals designate the same elements described above in conjunction with FIGS. 1-7. Upper and lower clamping arms 12 and 14 are flexibly connected by hinge element 16 at hinge points 20 and 18, respectively. Surfaces 22 and 24 of the clamp are adapted to contact and engage a blood vessel 26 (FIGS. 9, 10).

In this embodiment, the lateral dimension of upper clamping arm 12 is the same as that of lower clamping arm 14. A locking pawl 54, configured differently from locking pawl 28 of FIG. 1, is flexibly connected at hinge point 30 to the upper clamping arm 12. Pawl 54 includes an indented segment 56 which extends inward approximately half the thickness of locking pawl 54, and includes an entry 58 between a substantially V-shaped receiving portion 60 and a latch pin 62.

Receiving portion 60, which is the same thickness as upper clamping arm 12, extends over indented segment 56 and is adapted to receive the upwardly extending locking mechanism 64, which is flexibly hinged to lower clamping arm 38 at hinge point 38. As clamp 10 is closed, latch pin 62 glides over the outer surface 66 of locking mechanism 64 until it snaps into place at the underside 68 of the locking mechanism, adjacent hinge point 38, thereby locking the clamping arms together into a one piece rigid unitary assembly (FIGS. 9, 10).

Figure 2:
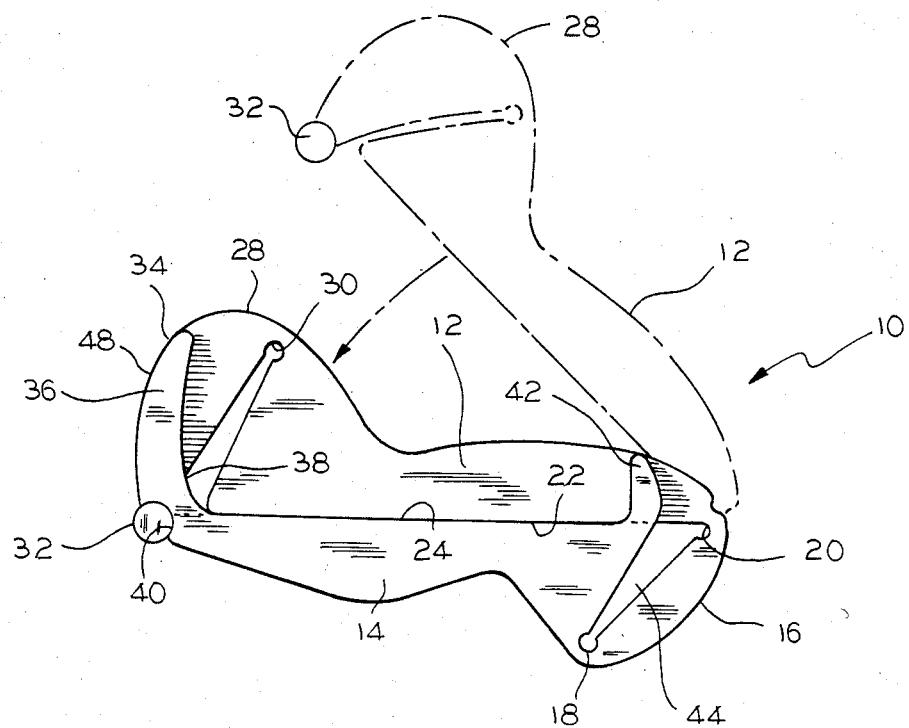
FIG. 2 is a side elevation view of the clamping device of FIG. 1, shown as it moves from an open to a closed and locked position.

As shown by dotted diagram 70 in FIG. 9, hinge points 18, 20, 30, and 38 form a parallelogram when the clamp 10 is closed over a blood vessel 26, in the same manner as described relating to the embodiment of FIGS. 1-3. Therefore, the operation of the clamping device of the second embodiment during a clamping operation is the same as described relative to the clamp of FIGS. 1-3, the primary difference in the second embodiment being the structure of the locking pawl 54 and locking mechanism 64.

FIGS. 9 and 10 show the different configurations of the clamping device 10 when a small vessel and a large vessel is clamped. Note that in FIG. 9, the angle A is significantly smaller than corresponding angle A in FIG. 10 due to the significantly smaller vessel illustrated in FIG. 9 as compared to FIG. 10. However, it should be further noted that the clamping surfaces 22, 24 of the respective clamping arms 12, 14 remain parallel to each other in FIGS. 9 and 10 regardless of the thickness of the blood vessel. Thus, the configuration of the parallelogram 70 has automatically changed from FIG. 9 to FIG. 10 since the distance t has become greater in the latter figure.

As described before, the parallel movement of the clamping arms 12, 14 during the final phases of the clamping operation enable the blood vessel to be clamped with a uniform pressure over its entire width as the clamp arms 12, 14 adjust themselves about the four hinge points and move parallel to one another to maintain a pre-determined pressure across the width of the vessel. This significantly reduces the possibility of damaging the vessel.

The embodiment of the invention disclosed in FIGS. 8-10 also includes a rear wall 72 depending from upper clamping arm 14. Wall 72 acts as a limiting stop for the blood vessel and prevents the vessel from being pinched during the early phases of the clamping operation when pressure to the blood vessel is applied over a gradually increasing area starting with the right side of clamp 10, as viewed in FIGS. 8-10.

A forward wall or abutment 74 is provided on lower clamping arm 14 adjacent the left or open end thereof, as illustrated in FIGS. 8-10, to provide a forward limit stop to prevent the blood vessel from being dislodged or rolling out of the left side of the clamp after the clamp has been moved to its closed position.

Locking mechanism 64 of the second embodiment of the invention is capable of pivoting ninety degrees counter-clockwise about hinge point 38 to provide a wider opening for positioning the clamp 10 around a blood vessel 26 in a restricted area. Once the clamp is properly placed straddling the vessel, locking mechanism 64 is rotated clockwise about hinge point 38, and the clamp is moved to its locking position as described above.

The clamps of each of the embodiments described herein can be fabricated simply and economically from a single piece of plastic or flexible material which provides the inherent "living hinges" at hinge points 18, 20, 30 and 38. Forward and rear walls are provided to prevent the blood vessel from being pinched, or from rolling out of the clamp. The novel four pivot point parallelogram structure which defines the relationship between the four hinge points during the clamping operation provides an automatically adjusting clamp that applies a pre-established measure of pressure to the blood vessel at all thicknesses of the blood vessel. The parallel motion of the clamping arms resulting from the four hinge point construction prevents accidental damage to the blood vessel due to the relatively uniform pressure application by the clamping arms.

Although several embodiments of the present invention have been described and illustrated, it will be apparent to those skilled in the art that various modifications may be made without departing from the principles of the invention, and such modifications are contemplated to be encompassed within the scope of the present invention.

I claim:

1. A surgical clamp for a blood vessel comprising first and second clamping arms adapted to come together to clamp said blood vessel, each of said clamping arms connected at one end thereof to a hinge element, said first arm being connected to said hinge element at a first hinge point, said second arm being connected to said hinge element at a second hinge point, the other end of one of said clamping arms having a locking pawl connected thereto at a third hinge point, said locking pawl being adapted to engage and interlock with a locking mechanism on the other end of the other of said clamping arms at a fourth hinge point, wherein said first, second, third and fourth hinge points are spaced apart from each other and are aligned in a parallelogram shaped configuration whereby the distance between said clamping arms is automatically adjusted to accomodate the thickness of the blood vessel being clamped as said clamping arms are brought together.

2. The surgical clamp of claim 1, wherein said surgical clamp comprises a single piece of plastic material.

3. The surgical clamp of claim 2, wherein said first, second and third hinge points are living hinges.

4. The surgical clamp of claim 1, including wall means depending from at least one of said clamping arms and extending between said hinge element and said one clamping arm to provide a wall which limits the movement of said blood vessel in said clamp toward said hinge element to prevent pinching of said blood vessel between said hinge element and one of said clamping arms.

5. The surgical clamp of claim 1, wherein said locking mechanism comprises upright locking arm means connected to said other clamping arm, an indentation adjacent the connection between said locking arm means and said other clamping arm, said indentation adapted to receive and engage a latch member on said locking pawl.

6. The surgical clamp of claim 5, wherein said upright locking arm means comprises forward wall surface means adjacent the other end of said clamping arms, whereby movement of said blood vessel between said clamping arms is limited in a direction toward said forward wall surface means, thereby preventing said clamped blood vessel from being accidentally dislodged from said surgical clamp during and subsequent to a clamping operation.

7. The surgical clamp of claim 1, wherein said locking mechanism is flexibly connected to said other of said clamping arms to enable said locking mechanism to be rotated approximately ninety degrees about said flexible connection to enable the blood vessel to be readily positioned between said clamping arms.

8. The surgical clamp of claim 4, wherein said other clamping arm is smaller in lateral dimension than said one clamping arm, and said other clamping arm is centrally connected to said hinge element to thereby axially engage substantially the central portion of said one clamping arm when both said clamping arms are brought together, said wall means comprising two spaced apart wall elements extending from said one clamping arm in a general direction toward said other clamping arm, said other clamping arm extending between said wall elements when said clamping arms are brought together.

9. The surgical clamp of claim 1, wherein said locking pawl comprises an indented segment, said locking mechanism flexibly connected to said other clamping arm in the path of travel of said indented portion such that when the clamping arms are brought together, the locking mechanism is received by said indented portion of said locking pawl.

10. A surgical clamp for a blood vessel comprising upper and lower clamping arms adapted to come together to clamp said blood vessel, each of said clamping arms flexibly connected at one end thereof to a hinge element at spaced apart hinge points, the other end of one of said clamping arms having a locking pawl flexibly connected thereto, a latch pin fixed to said locking pawl and spaced at a distance from said flexible connection between said locking pawl and said one clamping arm, the other end of the other of said clamping arms having a locking mechanism adapted to receive and engage said latch pin when said clamping arms are brought together, wherein the two spaced apart points of connection of said clamping arms to said hinge element, the point of engagement of said latch pin and said locking mechanism and the point of connection of said locking pawl to one of said clamping arms comprise four discrete points which are aligned to form a parallelogram configuration whereby the distance between said clamping arms is automatically adjusted to accomodate the thickness of the blood vessel being clamped as said clamping arms are brought together.

11. A surgical clamp for a blood vessel comprising an upper clamping arm, a lower clamping arm, facing clamping surfaces on each of said clamping arms, said lower clamping arm being flexibly connected at one end thereof to a hinge element at a first hinge point, said upper clamping arm being flexibly connected at one end thereof to said hinge element at a second hinge point, said first and second hinge points being spaced apart from each other, a locking pawl flexibly connected to one of said upper and lower clamping arms at a third hinge point at another end of said clamping arms, a locking mechanism flexibly connected to the other of said upper and lower clamping arms at said another end of said clamping arms and at a fourth hinge point, said locking pawl including a latch pin adapted to engage and be releasably held by said locking mechanism at said fourth hinge point when said upper and lower clamping arms are moved towards each other to clamp said blood vessel, said four hinge points arrayed in substantially a parallelogram configuration, whereby said four hinge points provide four pivot points for the upper and lower clamping arms thereby allowing the clamping arms to automatically adjust the distance between their respective clamping surfaces depending upon the thickness of the blood vessel as the clamp is applied to the blood vessel.

* * * * *